US011175295B2

(12) United States Patent
Miller et al.

(10) Patent No.: US 11,175,295 B2
(45) Date of Patent: Nov. 16, 2021

(54) ANTIBODIES AND METHODS FOR THE DETECTION OF CELL DEATH

(71) Applicant: Defined Diagnostics, LLC, Rockville, MD (US)

(72) Inventors: Jeffrey Allan Miller, Lincoln University, PA (US); Eddie Phillip Jeffries, Sterling, VA (US)

(73) Assignee: Defined Diagnostics, LLC, Rockville, MD (US)

( * ) Notice: Subject to any disclaimer, the term of this patent is extended or adjusted under 35 U.S.C. 154(b) by 0 days.

(21) Appl. No.: 16/514,380

(22) Filed: Jul. 17, 2019

(65) Prior Publication Data

US 2020/0041526 A1 Feb. 6, 2020

Related U.S. Application Data

(62) Division of application No. 15/127,644, filed as application No. PCT/US2015/021678 on Mar. 20, 2015, now Pat. No. 10,401,368.

(60) Provisional application No. 61/987,668, filed on May 2, 2014, provisional application No. 61/968,016, filed on Mar. 20, 2014.

(51) Int. Cl.
*G01N 33/68* (2006.01)
*C07K 16/18* (2006.01)
*G01N 33/543* (2006.01)

(52) U.S. Cl.
CPC ......... *G01N 33/6893* (2013.01); *C07K 16/18* (2013.01); *G01N 33/54333* (2013.01); *C07K 2317/33* (2013.01); *C07K 2317/34* (2013.01); *C07K 2317/56* (2013.01); *C07K 2317/72* (2013.01); *G01N 2333/4742* (2013.01); *G01N 2510/00* (2013.01); *G01N 2800/085* (2013.01); *G01N 2800/7033* (2013.01)

(58) Field of Classification Search
CPC ......... G01N 33/6893; G01N 33/54333; G01N 2800/085; G01N 2800/7033; G01N 2333/4742; G01N 2510/00; C07K 16/18; C07K 2317/72; C07K 2317/33; C07K 2317/34; C07K 2317/56
See application file for complete search history.

(56) References Cited

U.S. PATENT DOCUMENTS

| | | | |
|---|---|---|---|
| 4,208,479 A | 6/1980 | Zuk et al. | |
| 6,503,702 B1 | 1/2003 | Stewart | |
| 6,673,533 B1 | 1/2004 | Wohlstadter et al. | |
| 6,897,026 B2 | 5/2005 | Lamont et al. | |
| 2005/0032175 A1 | 2/2005 | Stahl et al. | |
| 2006/0292641 A1 | 12/2006 | Nakanishi et al. | |
| 2009/0221004 A1 | 9/2009 | Hong | |
| 2011/0201022 A1* | 8/2011 | Foehr ................. | G01N 33/6854 435/7.4 |
| 2013/0260388 A1 | 10/2013 | Shen et al. | |

FOREIGN PATENT DOCUMENTS

| | | |
|---|---|---|
| WO | WO 8202661 | 8/1982 |
| WO | WO 1994/10332 | 5/1994 |
| WO | WO 2011016238 | 2/2011 |
| WO | WO 2013082463 | 6/2013 |

OTHER PUBLICATIONS

Bost et al. (Immunol. Invest. 1988; 17:577-586) (Year: 1988).*
Bendayan (J. Histochem. Cytochem. 1995; 43:881-886) (Year: 1995).*
Campbell, A., "General properties and applications of monoclonal antibodies," Monoclonal Antibody Technology, Elsevier Publishing Company, 1984, pp. 1-29.
Communication pursuant to Rules 161(2) and 162 EPC for European Patent Appl.ication No. 15764318.0, dated Nov. 15, 2016.
Response to the Communication pursuant to Rules 161(2) and 162 EPC for European Patent Application No. 15764318.0, dated Nov. 15, 2016.
International Search Report for International Application No. PCT/US2015/021678, dated Jul. 2, 2015.
Written Opinion for International Application No. PCT/US2015/021678, dated Jun. 15, 2015.

* cited by examiner

*Primary Examiner* — Changhwa J Cheu
(74) *Attorney, Agent, or Firm* — Lewis J. Kreisler

(57) ABSTRACT

Disclosed herein are antibodies having binding specificity to the amino acid sequences Ala Ser Ser Gly Leu Thr Val Glu Val Asp (SEQ ID NO:1) and Thr Val Glu Val Asp (SEQ ID NO:14), and methods of detecting cell death in a sample, comprising contacting the sample with a first antibody specific for a C-terminal amino acid sequence Ala Ser Ser Gly Leu Thr Val Glu Val Asp (SEQ ID NO:1) or Thr Val Glu Val Asp (SEQ ID NO:14) of a CK18 protein fragment having a C-terminal amino acid sequence of Val Glu Val Asp (SEQ ID NO:2) and a second antibody that specifically binds an epitope that is present in both full-length CK18 and the CK18 protein fragment, and that does not overlap with SEQ ID NO:1 or SEQ ID NO:14, under conditions such that the CK18 protein fragment present in the sample specifically binds to the first antibody and the second antibody, wherein one of the antibodies is bound to a solid support and the other antibody is bound to a detection moiety capable of producing a signal; optionally removing any unbound or excess material; and detecting the signal from the detection moiety, wherein the signal is positively correlated with the presence of the CK18 protein fragment in the sample.

8 Claims, 9 Drawing Sheets

Specification includes a Sequence Listing.

SEQUENCE LISTING

```
<160> NUMBER OF SEQ ID NOS: 14

<210> SEQ ID NO 1
<211> LENGTH: 10
<212> TYPE: PRT
<213> ORGANISM: Human

<400> SEQUENCE: 1

Ala Ser Ser Gly Leu Thr Val Glu Val Asp
1               5                   10

<210> SEQ ID NO 2
<211> LENGTH: 4
<212> TYPE: PRT
<213> ORGANISM: Human

<400> SEQUENCE: 2

Val Glu Val Asp
1

<210> SEQ ID NO 3
<211> LENGTH: 430
<212> TYPE: PRT
<213> ORGANISM: Human

<400> SEQUENCE: 3

Met Ser Phe Thr Thr Arg Ser Thr Phe Ser Thr Asn Tyr Arg Ser Leu
1               5                   10                  15

Gly Ser Val Gln Ala Pro Ser Tyr Gly Ala Arg Pro Val Ser Ser Ala
            20                  25                  30

Ala Ser Val Tyr Ala Gly Ala Gly Gly Ser Gly Ser Arg Ile Ser Val
        35                  40                  45

Ser Arg Ser Thr Ser Phe Arg Gly Gly Met Gly Ser Gly Gly Leu Ala
    50                  55                  60

Thr Gly Ile Ala Gly Gly Leu Ala Gly Met Gly Gly Ile Gln Asn Glu
65                  70                  75                  80

Lys Glu Thr Met Gln Ser Leu Asn Asp Arg Leu Ala Ser Tyr Leu Asp
```

```
                    85                  90                  95
Arg Val Arg Ser Leu Glu Thr Glu Asn Arg Arg Leu Glu Ser Lys Ile
                100                 105                 110

Arg Glu His Leu Glu Lys Lys Gly Pro Gln Val Arg Asp Trp Ser His
                115                 120                 125

Tyr Phe Lys Ile Ile Glu Asp Leu Arg Ala Gln Ile Phe Ala Asn Thr
    130                 135                 140

Val Asp Asn Ala Arg Ile Val Leu Gln Ile Asp Asn Ala Arg Leu Ala
145                 150                 155                 160

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
                180                 185                 190

Asn Ile Thr Arg Leu Gln Leu Glu Thr Glu Ile Glu Ala Leu Lys Glu
                195                 200                 205

Glu Leu Leu Phe Met Lys Lys Asn His Glu Glu Glu Val Lys Gly Leu
                210                 215                 220

Gln Ala Gln Ile Ala Ser Ser Gly Leu Thr Val Glu Val Asp Ala Pro
225                 230                 235                 240

Lys Ser Gln Asp Leu Ala Lys Ile Met Ala Asp Ile Arg Ala Gln Tyr
                245                 250                 255

Asp Glu Leu Ala Arg Lys Asn Arg Glu Glu Leu Asp Lys Tyr Trp Ser
                260                 265                 270

Gln Gln Ile Glu Glu Ser Thr Thr Val Val Thr Thr Gln Ser Ala Glu
                275                 280                 285

Val Gly Ala Ala Glu Thr Thr Leu Thr Glu Leu Arg Arg Thr Val Gln
                290                 295                 300

Ser Leu Glu Ile Asp Leu Asp Ser Met Arg Asn Leu Lys Ala Ser Leu
305                 310                 315                 320

Glu Asn Ser Leu Arg Glu Val Glu Ala Arg Tyr Ala Leu Gln Met Glu
                325                 330                 335

Gln Leu Asn Gly Ile Leu Leu His Leu Glu Ser Glu Leu Ala Gln Thr
                340                 345                 350

Arg Ala Glu Gly Gln Arg Gln Ala Gln Glu Tyr Glu Ala Leu Leu Asn
                355                 360                 365

Ile Lys Val Lys Leu Glu Ala Glu Ile Ala Thr Tyr Arg Arg Leu Leu
                370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
                405                 410                 415

Lys Val Val Ser Glu Thr Asn Asp Thr Lys Val Leu Arg His
                420                 425                 430

<210> SEQ ID NO 4
<211> LENGTH: 238
<212> TYPE: PRT
<213> ORGANISM: Human

<400> SEQUENCE: 4

Met Ser Phe Thr Thr Arg Ser Thr Phe Ser Thr Asn Tyr Arg Ser Leu
1               5                   10                  15

Gly Ser Val Gln Ala Pro Ser Tyr Gly Ala Arg Pro Val Ser Ser Ala
                20                  25                  30
```

```
Ala Ser Val Tyr Ala Gly Ala Gly Gly Ser Gly Ser Arg Ile Ser Val
         35                  40                  45

Ser Arg Ser Thr Ser Phe Arg Gly Gly Met Gly Ser Gly Gly Leu Ala
 50                  55                  60

Thr Gly Ile Ala Gly Leu Ala Gly Met Gly Gly Ile Gln Asn Glu
 65                  70                  75                  80

Lys Glu Thr Met Gln Ser Leu Asn Asp Arg Leu Ala Ser Tyr Leu Asp
                 85                  90                  95

Arg Val Arg Ser Leu Glu Thr Glu Asn Arg Arg Leu Glu Ser Lys Ile
            100                 105                 110

Arg Glu His Leu Glu Lys Lys Gly Pro Gln Val Arg Asp Trp Ser His
        115                 120                 125

Tyr Phe Lys Ile Ile Glu Asp Leu Arg Ala Gln Ile Phe Ala Asn Thr
    130                 135                 140

Val Asp Asn Ala Arg Ile Val Leu Gln Ile Asp Asn Ala Arg Leu Ala
145                 150                 155                 160

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
            180                 185                 190

Asn Ile Thr Arg Leu Gln Leu Glu Thr Glu Ile Glu Ala Leu Lys Glu
        195                 200                 205

Glu Leu Leu Phe Met Lys Lys Asn His Glu Glu Val Lys Gly Leu
    210                 215                 220

Gln Ala Gln Ile Ala Ser Ser Gly Leu Thr Val Glu Val Asp
225                 230                 235

<210> SEQ ID NO 5
<211> LENGTH: 121
<212> TYPE: PRT
<213> ORGANISM: mouse

<400> SEQUENCE: 5

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Asn Gly Gly Ser Thr Ile Ile Tyr Tyr Ala Asp Thr Val
    50                  55                  60

Lys Gly Arg Phe Thr Val Ser Arg Asp Asn Pro Lys Asn Thr Leu Phe
65                  70                  75                  80

Leu Gln Met Thr Ser Leu Arg Ser Asp Asp Thr Ala Met Tyr Phe Cys
                85                  90                  95

Val Arg Arg Thr Pro Thr Ala Ala Gly Gly Ala Met Asp Tyr Trp Gly
            100                 105                 110

Gln Gly Thr Ser Val Thr Val Ser Ser
        115                 120

<210> SEQ ID NO 6
<211> LENGTH: 363
<212> TYPE: DNA
<213> ORGANISM: mouse

<400> SEQUENCE: 6
```

```
gatgtgcagc tggtggagtc tgggggaggc ttagtgcagc tggagggtc ccggaaactc    60 tcctgtgcag cctctggatt cactttcagt agttttggaa tgcactgggt tcgtcaggct   120
ccagagaagg ggctggaatg ggtcgcatac attaatggtg gcagtaccat catctactat   180
gcagacacag tgaagggccg attcaccgtc tccagagaca atcccaagaa caccctgttc   240
ctgcaaatga ccagtctaag gtctgacgac acggccatgt attttgtgt aagaaggacc    300 cctacggctg cgggggggc tatggactat tggggtcaag aacctcagt caccgtctcc    360 tca                                                                 363
```

<210> SEQ ID NO 7
<211> LENGTH: 112
<212> TYPE: PRT
<213> ORGANISM: mouse

<400> SEQUENCE: 7

```
Asn Ile Met Val Thr Gln Ser Pro Ser Ser Leu Ala Val Ser Ala Gly
1               5                   10                  15

Glu Lys Val Thr Met Thr Cys Lys Ser Ser Gln Ser Leu Phe Tyr Ser
            20                  25                  30

Ser Asn Gln Lys Asn Tyr Leu Ala Trp Phe Gln Lys Pro Gly Gln
        35                  40                  45

Ser Pro Lys Leu Leu Ile Tyr Trp Ala Ser Thr Arg Glu Ser Gly Val
    50                  55                  60

Ala Asp Arg Phe Thr Gly Ser Gly Tyr Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Tyr Leu Ser Ser Trp Thr Phe Gly Gly Gly Thr Lys Val Glu Ile Lys
            100                 105                 110
```

<210> SEQ ID NO 8
<211> LENGTH: 337
<212> TYPE: DNA
<213> ORGANISM: mouse

<400> SEQUENCE: 8

```
aacattatgg tgacacagtc gccatcatct ctggctgtgt ctgcaggaga aaaggtcact    60
atgacctgta gtccagtca agtcttttc tacagttcaa accagaagaa ctacttggcc    120
tggttccagc agaaaccagg gcagtctcct aaactgctga tctactgggc atccactagg   180
gagtctggtg tcgctgatcg cttcacaggc agtggatatg gcacagattt tactctaacc   240
atcagcagtg tacaggccga agacctggca gtttattact gtcaacaata cctctcgtct   300
tggacgttcg gtggaggtac caaggtggaa atcaaac                            337
```

<210> SEQ ID NO 9
<211> LENGTH: 4
<212> TYPE: PRT
<213> ORGANISM: human

<400> SEQUENCE: 9

Asp Ala Leu Asp
1

<210> SEQ ID NO 10
<211> LENGTH: 10
<212> TYPE: PRT
<213> ORGANISM: human

```
<400> SEQUENCE: 10

Ala Pro Lys Ser Gln Asp Leu Ala Lys Ile
1               5                   10

<210> SEQ ID NO 11
<211> LENGTH: 9
<212> TYPE: PRT
<213> ORGANISM: human

<400> SEQUENCE: 11

Pro Lys Ser Gln Asp Leu Ala Lys Ile
1               5

<210> SEQ ID NO 12
<211> LENGTH: 9
<212> TYPE: PRT
<213> ORGANISM: human

<400> SEQUENCE: 12

Ala Ser Ser Gly Leu Thr Val Glu Val
1               5

<210> SEQ ID NO 13
<211> LENGTH: 10
<212> TYPE: PRT
<213> ORGANISM: human

<400> SEQUENCE: 13

Glu Asp Phe Asn Leu Gly Asp Ala Leu Asp
1               5                   10

<210> SEQ ID NO 14
<211> LENGTH: 5
<212> TYPE: PRT
<213> ORGANISM: human

<400> SEQUENCE: 14

Thr Val Glu Val Asp
1               5
```

ANTIBODIES AND METHODS FOR THE DETECTION OF CELL DEATH

CROSS-REFERENCE TO RELATED PATENT APPLICATIONS

This application is a divisional of U.S. application Ser. No. 15/127,644, filed Sep. 20, 2016, a national stage application of International Application No. PCT/US2015/021678, filed internationally on Mar. 20, 2015, which claims priority to U.S. Provisional Patent Application Nos. 61/968,016, filed Mar. 20, 2014, and 61/987,668, filed May 2, 2014. The contents of each of the above-references applications are hereby incorporated by reference in their entireties.

FIELD

The present disclosure relates to the detection of cell death. In particular, the present disclosure relates to antibodies and assay methods used to detect cell death.

BACKGROUND

Apoptosis is the process of programmed cell death (PCD) that may occur in multicellular organisms. Biochemical events lead to characteristic cell changes (morphology) and death. These changes include blebbing, cell shrinkage, nuclear fragmentation, chromatin condensation, and chromosomal DNA fragmentation. In addition to its importance as a biological phenomenon, defective apoptotic processes have been implicated in an extensive variety of diseases. Excessive apoptosis causes atrophy, whereas an insufficient amount results in uncontrolled cell proliferation, such as cancer.

Caspases are proteins that are highly conserved, cysteine-dependent, aspartate-specific proteases. There are two types of caspases: initiator caspases, caspase 2, 8, 9, and 10, and effector caspases, caspase 3, 6 and 7. The activation of initiator caspases requires binding to specific oligomeric adaptor protein. Effector caspases are then activated by these active initiator caspases through proteolytic cleavage. The active effector caspases then proteolytically degrade a host of intracellular proteins to carry out the cell death program.

Detection and measurement of apoptosis has been found to be useful in detecting the presence or severity of diseases. Cytokeratins (CK) are known to be useful markers for many different diagnostic methods. For example, circulating fragments of cytokeratin 18 (also CK18, CK-18, K18, or K-18), a cytoskeletal marker of cell death, such as hepatocyte death, have been shown in several studies to indicate the transition from benign fatty liver to nonalcoholic steatohepatitis (NASH), with a risk of fibrosis, in patients with nonalcoholic fatty liver disease (NAFLD).

NAFLD is a spectrum of disorders characterized by hepatic steatosis, which may be benign (nonalcoholic fatty liver or NAFL) or which may progress via inflammation and fibrosis to NASH followed by cirrhosis and liver failure. Liver biopsy, the standard diagnostic approach for NAFL/NASH, has limitations due to sampling site variability, cost and procedure-related morbidity. Appropriate circulating biomarkers may enable diagnosis, staging and monitoring of NAFL/NASH with fewer biopsies.

Assays incorporating CK18 as a biomarker may be developed to monitor the severity of such diseases by measuring apoptosis. CK18 is also useful for detecting and monitoring other liver diseases including hepatitis, biliary sclerosis, and poisoning. CK18 is also useful for quantifying cell death in cancer and diseases that are part of the metabolic syndrome, including degenerative diseases, such as cardiovascular and liver disease.

This disclosure covers antibodies and related assays and methods for detecting cell death by measuring the presence of CK18 fragments, that are typically present only when a cell is dying and after full-length CK18 is exposed to and cleaved by caspases.

SUMMARY

The disclosure relates generally to antibodies having binding specificity to the amino acid sequence Ala Ser Ser Gly Leu Thr Val Glu Val Asp (SEQ ID NO:1). The disclosure also relates generally to antibodies having binding specificity to the amino acid sequence Thr Val Glu Val Asp (SEQ ID NO:14).

The disclosure relates generally to methods of producing an antibody that binds selectively to a cytokeratin 18 (CK18) protein fragment having a C-terminal amino acid sequence of Val Glu Val Asp (SEQ ID NO:2), comprising immunizing a mammal with an antigen having a C-terminal amino acid sequence of Ala Ser Ser Gly Leu Thr Val Glu Val Asp (SEQ ID NO:1) or Thr Val Glu Val Asp (SEQ ID NO:14) and isolating the antibody.

The disclosure relates generally to methods of producing an antibody that binds selectively to a cytokeratin 18 (CK18) protein fragment having a C-terminal amino acid sequence of Val Glu Val Asp (SEQ ID NO:2), comprising immunizing a mammal with an antigen having a C-terminal amino acid sequence of Ala Ser Ser Gly Leu Thr Val Glu Val Asp (SEQ ID NO:1) or Thr Val Glu Val Asp (SEQ ID NO:14) and generating a cell line producing a monoclonal antibody.

The disclosure relates generally to methods of detecting cell death and/or a cytokeratin 18 (CK18) protein fragment having a C-terminal amino acid sequence of Val Glu Val Asp (SEQ ID NO:2) in a sample, comprising the steps of contacting the sample with a first antibody specific for a C-terminal amino acid sequence Ala Ser Ser Gly Leu Thr Val Glu Val Asp (SEQ ID NO:1) of the CK18 protein fragment or for a C-terminal amino acid sequence Thr Val Glu Val Asp (SEQ ID NO:14) of the CK18 protein fragment and a second antibody that specifically binds an epitope that is present in both full-length CK18 and the CK18 protein fragment, and that does not overlap with SEQ ID NO:1 or SEQ ID NO:14, under conditions such that the CK18 protein fragment present in the sample specifically binds to the first antibody and the second antibody, wherein one of the antibodies is bound to a solid support and the other antibody is bound to a detection moiety capable of producing a signal; optionally removing any unbound or excess material; and detecting the signal from the detection moiety, wherein the signal is positively correlated with the presence of the CK18 protein fragment in the sample.

The disclosure relates generally to methods of determining the occurrence of cell death in a sample, comprising the steps of combining the sample with a first antibody that has binding specificity to the amino acid sequence Ala Ser Ser Gly Leu Thr Val Glu Val Asp (SEQ ID NO:1) or to the amino acid sequence Thr Val Glu Val Asp (SEQ ID NO:14) and a second antibody that specifically binds an epitope that is present in both full-length CK18 and a CK18 protein fragment having a C-terminal amino acid sequence of Val Glu Val Asp (SEQ ID NO:2), and that does not overlap with SEQ ID NO:1 or SEQ ID NO:14, under conditions such that the CK18 protein fragment present in the sample specifically binds to the first antibody and the second antibody, wherein one of the antibodies is bound to a solid support and the other antibody is bound to a detection moiety; performing an immunological assay using the first antibody and second antibody; determining the presence in the sample of a caspase-cleaved cytokeratin 18 (CK18) protein fragment having a C-terminal amino acid sequence of Val Glu Val Asp (SEQ ID NO:2), wherein the presence of the CK18 protein fragment is positively correlated to cell death. The determining step further comprising detecting a signal from the detection moiety attached to one of the antibodies, wherein detection of the signal is positively correlated with the presence of the CK18 protein fragment.

The disclosure generally relates to kits for detecting a cytokeratin 18 (CK18) protein fragment having a C-terminal amino acid sequence of Val Glu Val Asp (SEQ ID NO:2) in a sample, the kit comprising a solid support; a detection moiety; a first antibody specific for a C-terminal amino acid sequence Ala Ser Ser Gly Leu Thr Val Glu Val Asp (SEQ ID NO:1) of the CK18 protein fragment; or for a C-terminal amino acid sequence Ala Ser Ser Gly Leu Thr Val Glu Val Asp (SEQ ID NO:1) of the CK18 protein fragment; a second antibody that specifically binds an epitope that is present in both full-length CK18 and the CK18 protein fragment, and that does not overlap with SEQ ID NO:1 or SEQ ID NO:14; and instructions for performing the detection assay.

Apart from the subject matter discussed above, the present disclosure includes a number of other exemplary features such as those explained hereinafter. It is to be understood that both the foregoing description and the following description are exemplary only.

BRIEF DESCRIPTION OF THE SEQUENCES

SEQ ID NO:1 is a C-terminal amino acid sequence ($^{229}$ASSGLTVEVD) of a cytokeratin 18 (CK18) protein fragment.

SEQ ID NO:2 is the C-terminal amino acid sequence ($^{235}$VEVD) of the caspase-cleaved fragment of SEQ ID NO:3 and SEQ ID NO:4.

SEQ ID NO:3 is the amino acid sequence of full-length human cytokeratin 18 (CK18) protein.

SEQ ID NO:4 is the amino acid sequence of a caspase-cleaved fragment (M1-D238) of cytokeratin 18 (CK18) protein, also referred to as "fragment B."

SEQ ID NO:5 is the amino acid sequence of the variable region of the heavy chain of mAb 3C2.

SEQ ID NO:6 is the nucleotide sequence of the variable region of the heavy chain of mAb 3C2.

SEQ ID NO:7 is the amino acid sequence of the variable region of the light chain of mAb 3C2.

SEQ ID NO:8 is the nucleotide sequence of the variable region of the light chain of mAb 3C2.

SEQ ID NO:9 is the amino acid sequence $^{394}$DALD.

SEQ ID NO:10 is the amino acid sequence ($^{239}$APKSQD-LAKI) of a CK18 peptide.

SEQ ID NO:11 is the amino acid sequence ($^{240}$PKSQD-LAKI) of a CK18 peptide.

SEQ ID NO:12 is the amino acid sequence ($^{229}$AS-SGLTVEV) of a CK18 peptide.

SEQ ID NO:13 is the amino acid sequence ($^{388}$EDFNLGDALD) of a CK18 peptide.

SEQ ID NO:14 is the C-terminal amino acid sequence ($^{235}$TVEVD) of the caspase-cleaved fragment of SEQ ID NO:3 and SEQ ID NO:4.

BRIEF DESCRIPTION OF THE DRAWINGS

The accompanying table and figures are incorporated in, and constitute a part of this specification.

DETAILED DESCRIPTION

Definitions

Figure 1:
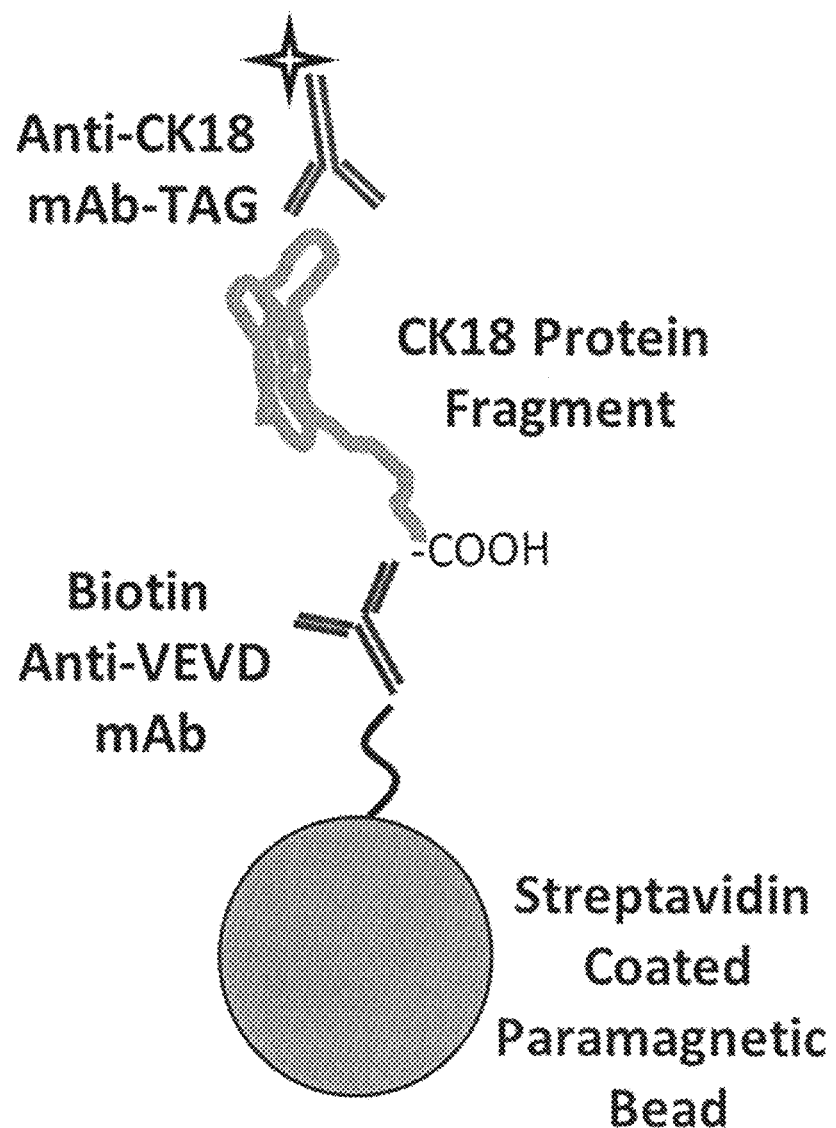
FIG. 1 is a schematic drawing of an assay format of an embodiment disclosed herein.

Unless specifically defined otherwise herein, all technical, scientific, and other terms used herein have the same meaning as commonly understood by one of ordinary skill in the art of immunoassays and related sciences.

The term "detection moiety" as used herein, refers to a moiety that is detectable and/or capable of producing a detectable signal, and can be attached, directly or indirectly, to various binding partners for detection in an assay.

The term "solid support" as used herein, refers to any material that is insoluble and/or has structural rigidity and resistance to changes of shape or volume, and to which a binding partner, such as an antibody, can be immobilized or bound.

"N-terminus," "N-terminal" or "amino terminus" refers to the amino acid residues which are closest to the amino-terminus of a protein.

"C-terminus," "C-terminal" or "carboxy terminus" refers to the amino acid residues which are closest to the carboxy-terminus of a protein.

Antibodies

Human cytokeratin protein CK18 is a 430 amino acid protein (SEQ ID NO:3) which may be fragmented by the activity of the proteases caspase 3 and caspase 6 during cell death or cellular apoptosis. This activity generates three protein fragments having the sequences M1-D238 (SEQ ID NO:4) (also referred to as "Fragment B"), A239-D397 and S398-H430 (sequences not provided). It is believed that detection of CK18 protein fragments having the C-terminal sequence VEVD (or Val Glu Val Asp) (SEQ ID NO:2) may be used as an indication of cell death, which may be useful in detection and diagnosis of degenerative diseases and cancer. Accordingly, one aspect of the present disclosure is directed to an antibody to a CK18 protein fragment having the C-terminal sequence of SEQ ID NO:2.

Another aspect of the present disclosure is directed to an antibody which specifically binds to the amino acid sequence Ala Ser Ser Gly Leu Thr Val Glu Val Asp (SEQ ID NO:1), or a functionally equivalent sequence. Another aspect of the present disclosure is directed to an antibody which specifically binds to the amino acid sequence Thr Val Glu Val Asp (SEQ ID NO:14), or a functionally equivalent sequence. The functionally equivalent sequences should include at least the sequence Val Glu Val Asp (SEQ ID NO:2). A functionally equivalent sequence refers to a sequence that is homologous in function, comprising at least the C-terminal amino acid sequence Val Glu Val Asp (SEQ ID NO:2) having replacements of one or several amino acids in the above identified amino acid sequences (SEQ ID NO:1 and SEQ ID NO:14) with other amino acids, other molecular forms of the amino acids, non-natural amino acids and/or derivatives, as long as the three-dimensional structure of the SEQ ID NO:1 or the SEQ ID NO:14 is mimicked.

In some embodiments, the antibody has binding specificity to the amino acid sequence Ala Ser Ser Gly Leu Thr Val Glu Val Asp (SEQ ID NO:1), and has a variable region of the heavy chain amino acid sequence of SEQ ID NO:5, and a variable region of the light chain amino acid sequence of SEQ ID NO:7. In some embodiments, the antibody has binding specificity to the amino acid sequence Ala Ser Ser Gly Leu Thr Val Glu Val Asp (SEQ ID NO:1), and has a variable region of the heavy chain nucleotide sequence of SEQ ID NO:6, and a variable region of the light chain nucleotide sequence of SEQ ID NO:8.

In some embodiments, the antibody has binding specificity to the amino acid sequence Thr Val Glu Val Asp (SEQ ID NO:14), and has a variable region of the heavy chain amino acid sequence of SEQ ID NO:5, and a variable region of the light chain amino acid sequence of SEQ ID NO:7. In some embodiments, the antibody has binding specificity to the amino acid sequence Thr Val Glu Val Asp (SEQ ID NO:14), and has a variable region of the heavy chain nucleotide sequence of SEQ ID NO:6, and a variable region of the light chain nucleotide sequence of SEQ ID NO:8.

The sequence Val Glu Val Asp (SEQ ID NO:2) is uncleaved within intact, full-length CK18 proteins such that full-length CK18 proteins do not react with an antibody having binding specificity for the sequences referenced above (i.e., SEQ ID NO:1, SEQ ID NO:2 and SEQ ID NO:14). This is significant for measuring cell death where, in such instances, the CK18 protein has been cleaved by caspases.

Another aspect of the present disclosure is directed to a second antibody that binds to an epitope that is present in (1) full-length CK18; (2) a CK18 protein fragment having the C-terminal sequence VEVD (SEQ ID NO:2); or (3) both (1) and (2), where the epitope has a different amino acid sequence from SEQ ID NO:1 and SEQ ID NO:14, i.e., little to no overlap with the amino acids in SEQ ID NO:1 and SEQ ID NO:14. The second antibody may be, for example, any suitable or commercially available monoclonal antibody. The second antibody may be used to identify and confirm the presence of the CK18 protein fragment having the C-terminal sequence VEVD (SEQ ID NO:2).

Antibody Development

Monoclonal antibodies may be developed to particular epitopes/antigens of the cytokeratin 18 protein and cytokeratin 18 protein fragments. These monoclonal antibodies may be used in Western blots, the development of ELISAs (enzyme-linked immunosorbent assays), as well as in the development of other assay formats including electrochemiluminescence (ECL)-based assays, for different forms of CK18 that are found, for example, in body fluids, such as blood, plasma, serum, etc. Standard procedures known to one of skill in the art may be used to generate hybridomas, which may produce monoclonal antibodies directed against the protein or peptide of interest.

One aspect of the present disclosure is directed to methods of developing antibodies that bind selectively to a CK18 protein fragment having a C-terminal amino acid sequence of Val Glu Val Asp (SEQ ID NO:2). In some embodiments, antibodies that bind selectively to a CK18 protein fragment having a C-terminal amino acid sequence of Val Glu Val Asp (SEQ ID NO:2) may be developed by immunizing a mammal with an antigen having a C-terminal amino acid sequence of Ala Ser Ser Gly Leu Thr Val Glu Val Asp (SEQ ID NO:1) or Thr Val Glu Val Asp (SEQ ID NO:14) and isolating the antibody.

In other embodiments, antibodies that bind selectively to a CK18 protein fragment having a C-terminal amino acid sequence of Val Glu Val Asp (SEQ ID NO:2) may be developed by immunizing a mammal with an antigen having a C-terminal amino acid sequence of Ala Ser Ser Gly Leu Thr Val Glu Val Asp (SEQ ID NO:1) or Thr Val Glu Val Asp (SEQ ID NO:14) and generating a cell line producing a monoclonal antibody.

Assay Development and Methods

The antibodies disclosed herein may be used in various formats of assays and methods that measure, quantify, and/or detect the presence of cell death as well as CK18 protein fragments having the C-terminal sequence of Val Glu Val Asp (SEQ ID NO:2). FIG. 1 is a schematic drawing of an assay format of an embodiment disclosed herein. The antibodies described herein can be combined with a sample to perform the assays. The sample may be a biological sample, such as tissue extracts, tissues used in immunohistochemistry, or fluids. The fluid samples may be derived from blood, plasma, serum, ascites fluid, saliva, sputum or urine.

The antibodies described herein may be linked or bound to various components or moieties in order to perform assay functions. For example, in some embodiments, the antibodies discussed herein may be bound directly through covalent or non-covalent attachment, or indirectly to a solid support or carrier. When bound indirectly, intermediate linkers may be used to bind the components. Suitable intermediate linkers include, but are not limited to, an amino group or a carboxylate group, biotin, ligands, or other chemical bonds. Suitable solid supports or carriers include, but are not limited to, glass surfaces (e.g., a glass slide or bead), plastic surfaces, metal surfaces, polystyrene surfaces (e.g., a bead or a plate), nitrocellulose surfaces, microparticles, nanoparticle surfaces, plates, wells, disposable ECL electrodes, and paramagnetic or magnetic beads that may be coated with avidin or streptavidin or have other surface functionalities to promote binding affinity. In FIG. 1, a streptavidin-coated paramagnetic bead is depicted as bound to a biotin-linked anti-VEVD mAb.

In some embodiments, the antibodies discussed herein may be linked or bound, directly through covalent or non-covalent attachment, or indirectly, to a detection moiety. When bound indirectly, intermediate linkers may be used as discussed herein. In some embodiments, the detection moiety may be any detection moiety that corresponds to a suitable detection method. FIG. 1 depicts an anti-CK18 mAB bound to TAG, an ECL detection moiety used in ECL-based detection methods.

Suitable detection moieties include, but are not limited to, electrochemiluminescence labels or compounds, chemiluminescent compounds, enzyme labels, fluorophores, chromogenic compounds, radiolabels, catalysts, colorimetric compounds or labels, labeled antibodies, a latex particle, a magnetic or paramagnetic particle, a radioactive element, fluorescent dyes, phosphorescent dyes, dye crystals, gold particles, silver colloidal particles, selenium colloidal particles, metal chelates, coenzymes, electro active groups, oligonucleotides or stable radicals. The metal chelate may be a ruthenium, an osmium or a europium metal chelate. The detection method may include any known detection method including, but not limited to, chromogenic, radioisotopic, fluorescence, immunofluorescence, luminescence, bioluminescence, and electrochemiluminescence (ECL).

In some embodiments, the detection method may be electrochemiluminescence (ECL). An electrochemiluminescent compound may serve as the detection moiety that may be detected or quantified within an ECL reaction chamber, such as in a flow cell, or on a disposable electrode. The solid support may serve to hold the antibody bound to the detection moiety near an ECL electrode in the ECL reaction chamber during detection.

Electrochemiluminescence (ECL) is the process whereby a molecular species, such as an "ECL label," luminesces upon the exposure of that species to electrochemical energy in an appropriate surrounding chemical environment. ECL is a rapid and sensitive bio-analytical detection technique that is a regenerative process. Some of the advantages achieved with ECL as a detection method in biological sample analysis include simpler, less expensive instrumentation; stable, nonhazardous labels; and increased assay performance characteristics such as lower detection limits, higher signal to noise ratios, and lower background levels. Certain applications of ECL have been developed and reported in the literature. U.S. Pat. Nos. 5,147,806, 5,068,808, 5,061,445, 5,296,191, 5,247,243, 5,221,605, 5,238,808, 5,310,687, 5,714,089, 6,165,729, 6,316,607, 6,808,939, 6,881,589, 6,881,536, and 7,553,448, the disclosures of which are incorporated herein by reference, detail certain methods, apparatuses, chemical moieties, inventions, and associated advantages of ECL.

Electrochemiluminescence signals are generated by a redox reaction between an electrochemiluminescent detection moiety, such as an ECL-active label with a redox substrate that occurs at the surface of an electrode. In certain embodiments, the ECL label is a ruthenium (Ru)-containing reagent. One example of a suitable electrochemiluminescent label is Tris(bypyridine)ruthenium(II) ([Ru(bipy)3]$^{2+}$), also referred to as TAG (See, e.g., FIG. 1). In some embodiments, the redox substrate is tripropylamine (TPA).

In some embodiments, a magnet usually positioned below an electrode may attract the paramagnetic beads, pulling down the Ru-labeled complex near the electrode. The Ru may then be oxidized. Oxidized tripropylamine (TPA) may react with the oxidized Ru, which then may emit a photon. The redox reaction between Ru and the redox substrate tripropylamine (TPA) that occurs only in the electric field near the electrode may be a regenerative process during continued application of voltage, which allows for an ECL signal that undergoes amplification over time. Because photons can only be generated near the electrode surface, electrochemiluminescence only occurs when the Ru is brought into proximity with the electrode by the magnet, thereby reducing background levels. Nonspecific ECL is not triggered by any known natural constituents of biological samples; therefore, unlike chemiluminescence, which often displays background artifacts due to nonspecific triggering of chemiluminescent detector molecules, ECL maintains reduced background levels.

In some embodiments, the solid support and/or the detection moiety may be from a lyophilized composition that is rehydrated with the sample for use in an assay. The lyophilized composition may contain standard and/or other necessary assay specific components of an assay, such as buffers, reagents, detergents, preservatives, salts, proteins, antibodies, etc. It is contemplated that the solid support and the detection moiety may be lyophilized in separate compositions, and then rehydrated with the sample. It is also contemplated that the solid support and the detection moiety may be lyophilized in the same composition, and then rehydrated with the sample. It is further contemplated that the lyophilized compositions disclosed herein may be rehydrated by one or more other assay specific components discussed herein.

The antibodies of the present disclosure may be used in various assay formats, including, for example, enzyme-linked immunosorbent assays (ELISA), enzyme-linked immunoparticle assays (ELIPA) or ECL assays for detecting cell death or the presence of CK18 fragments. In one aspect of the present disclosure, the assay method steps for detecting a cytokeratin 18 (CK18) protein fragment having an amino acid sequence of Val Glu Val Asp (SEQ ID NO:2) in a sample may include contacting the sample with a first antibody specific for a C-terminal amino acid sequence Ala Ser Ser Gly Leu Thr Val Glu Val Asp (SEQ ID NO:1) of the CK18 protein fragment and a second antibody that specifically binds an epitope that is present in both full-length CK18 and the CK18 protein fragment, and that does not overlap with SEQ ID NO:1, under conditions such that the CK18 protein fragment present in the sample specifically binds to the first antibody and the second antibody, wherein one of the antibodies is bound to a solid support and the other antibody is bound to a detection moiety capable of producing a signal; optionally removing any unbound or excess material, such as the sample, assay reagents, antibodies or protein fragments; and detecting the signal from the detection moiety, wherein the signal is positively correlated with the presence of the CK18 protein fragment in the sample.

In another aspect of the present disclosure, the assay method steps for detecting a cytokeratin 18 protein fragment having an amino acid sequence of Val Glu Val Asp (SEQ ID NO:2) in a sample may include contacting the sample with a first antibody specific for a C-terminal amino acid sequence Thr Val Glu Val Asp (SEQ ID NO:14) of the CK18 protein fragment and a second antibody that specifically binds an epitope that is present in both full-length CK18 and the CK18 protein fragment, and that does not overlap with SEQ ID NO:14, under conditions such that the CK18 protein fragment present in the sample specifically binds to the first antibody and the second antibody, wherein one of the antibodies is bound to a solid support and the other antibody is bound to a detection moiety capable of producing a signal; optionally removing any unbound or excess material, such as the sample, assay reagents, antibodies or protein fragments; and detecting the signal from the detection moiety, wherein the signal is positively correlated with the presence of the CK18 protein fragment in the sample.

In some embodiments, the first antibody may be bound to a solid support and the second antibody may be bound to a detection moiety. In other embodiments, the first antibody may be bound to a detection moiety and the second antibody may be bound to a solid support.

In one aspect of the present disclosure, the assay method steps for determining the occurrence of cell death in a sample may include combining the sample with a first antibody that has binding specificity to the C-terminal amino acid sequence Ala Ser Ser Gly Leu Thr Val Glu Val Asp (SEQ ID NO:1) and a second antibody that specifically binds an epitope that is present in both full-length CK18 and a CK18 protein fragment having a C-terminal amino acid sequence of Val Glu Val Asp (SEQ ID NO:2), and that does not overlap with SEQ ID NO:1, under conditions such that the CK18 protein fragment present in the sample specifically binds to the first antibody and the second antibody, wherein one of the antibodies is bound to a solid support and the other antibody is bound to a detection moiety; performing an immunological assay using the first antibody and the second antibody; determining the presence in the sample of a caspase-cleaved cytokeratin 18 protein fragment having a C-terminal amino acid sequence of Val Glu Val Asp (SEQ ID NO:2), wherein the presence of the CK18 protein fragment is positively correlated to cell death.

In another aspect of the present disclosure, the assay method steps for determining the occurrence of cell death in a sample may include combining the sample with a first antibody that has binding specificity to the C-terminal amino acid sequence Thr Val Glu Val Asp (SEQ ID NO:14) and a second antibody that specifically binds an epitope that is present in both full-length CK18 and a CK18 protein fragment having a C-terminal amino acid sequence of Val Glu Val Asp (SEQ ID NO:2), and that does not overlap with SEQ ID NO:14, under conditions such that the CK18 protein fragment present in the sample specifically binds to the first antibody and the second antibody, wherein one of the antibodies is bound to a solid support and the other antibody is bound to a detection moiety; performing an immunological assay using the first antibody and the second antibody; determining the presence in the sample of a caspase-cleaved cytokeratin 18 protein fragment having a C-terminal amino acid sequence of Val Glu Val Asp (SEQ ID NO:2), wherein the presence of the CK18 protein fragment is positively correlated to cell death.

In some embodiments, the first antibody may be bound to a solid support and the second antibody may be bound to a detection moiety. In other embodiments, the first antibody may be bound to a detection moiety and the second antibody may be bound to a solid support.

In some embodiments, the determining step may also include detecting a signal from the detection moiety attached to one of the antibodies, wherein detection of the signal is positively correlated with the presence of the CK18 protein fragment.

In some embodiments, the change in the amount of cell death may be determined. The determined change in the amount of cell death or cell apoptosis may be used in the diagnosis of diseases with involvement of apoptosis. The determined change in the amount of cell death may also be used in the monitoring of an effect of therapy of diseases with involvement of apoptosis. Such diseases may include cancer or degenerative diseases, such as cardiovascular and liver disease.

It is contemplated that the steps of the methods of the present disclosure do not have to be completed in the order provided herein, and may be performed in different orders, where, for example, the antibodies may be added to or contacted with the sample sequentially or at the same time. It is contemplated that the first antibody may be added first, followed by the addition of the second antibody, or the second antibody may be added first, followed by the addition of the first antibody.

If the antibodies are added sequentially, it is contemplated that the sample may be incubated for a period of time after the addition of each antibody and before the next method step(s). Additionally, the sample may be incubated for a period of time before the washing step and removal of any unbound or excess materials. It is further contemplated that additional washing steps to remove materials during the assay may be performed at additional times during the method, such as after the addition of each antibody, after the addition of both antibodies together and/or before the detecting step.

Kits

Another aspect of the present disclosure is directed to kits for performing the methods described herein. For example, a kit may be used for detecting cell death in a sample and/or a cytokeratin 18 (CK18) protein fragment having a C-terminal amino acid sequence of Val Glu Val Asp (SEQ ID NO:2) in a sample. Materials to be included in the kit may vary depending on the ultimate purpose. As such, the kits may include one or more components that are used in the methods.

The kits disclosed herein may include one or more of the following components: an antibody specific for a C-terminal amino acid sequence Ala Ser Ser Gly Leu Thr Val Glu Val Asp (SEQ ID NO:1) of the CK18 protein fragment; an antibody specific for a C-terminal amino acid sequence Thr Val Glu Val Asp (SEQ ID NO:14) of the CK18 protein fragment; an antibody to a CK18 protein fragment having the C-terminal sequence VEVD (or Val Glu Val Asp) (SEQ ID NO:2); an antibody that specifically binds an epitope that is present in both full-length CK18 and a CK18 protein fragment having the C-terminal sequence VEVD (SEQ ID NO:2), and that does not overlap with SEQ ID NO:1 or SEQ ID NO:14; a detection moiety; a solid support; assay reagents; buffers; standards and instructions for performing the methods disclosed herein, as well as other components and elements of the methods described herein. The standards can be additional chemical reagents or data (empirical) in printed or electronic form necessary for the calibration needed for performance of the assay.

The kit may include a vehicle within which some or all of the components are stored, carried or used for processing, such as a disposable cartridge. The kit may also include the use of an analyzer instrument, such as an ECL analyzer, and include instructions for use and related instrument components, such as cartridges used with the analyzer instrument.

The present disclosure can be better understood by reference to the examples included herein, which illustrate but do not limit the present teachings described herein. It is to be understood that both the descriptions disclosed herein and the following examples are merely illustrative and intended to be non-limiting.

EXAMPLES

The following examples are intended to be non-restrictive and explanatory only.

Example 1—3C2 Antibody Selection

Caspases 3 and 6 generated three CK18 protein fragments having the sequences M1-D238 (SEQ ID NO:4), A239-D397 and S398-H430. A monoclonal antibody specific for the carboxy terminus of human caspase-cleaved cytokeratin CK18 protein fragment having amino acids M1-D238 (SEQ ID NO:4) was generated by immunizing mice with a short peptide sequence of $^{229}$ASSGLTVEVD (SEQ ID NO:1) (designated as peptide P1 for the Examples). Mouse sera were screened for a positive response to peptide P1. Splenocytes from mice with a positive response were fused with myeloma cells and cell culture fluid from the resulting hybridomas screened against peptide P1. Supernatant from hybridoma cells producing antibody with a positive response to peptide P1 were further screened by an electrochemiluminescence (ECL) assay against biotin conjugated peptides $^{239}$APKSQDLAKI (SEQ ID NO:10), $^{240}$PKSQDLAKI (SEQ ID NO:11), $^{229}$ASSGLTVEVD (SEQ ID NO:1) and $^{229}$ASSGLTVEV (SEQ ID NO:12), which were each bound to streptavidin coated paramagnetic beads. Peptides $^{229}$ASSGLTVEVD (SEQ ID NO:1) and $^{229}$ASSGLTVEV (SEQ ID NO:12) represent the amino acid sequences A229-D238 and A229-V237 of cytokeratin 18 protein while peptides $^{239}$APKSQDLAKI (SEQ ID NO:10) and $^{240}$PKSQDLAKI (SEQ ID NO:11) represent the amino acid sequences A239-I248 and K240-I248 of cytokeratin 18.

Figure 2:
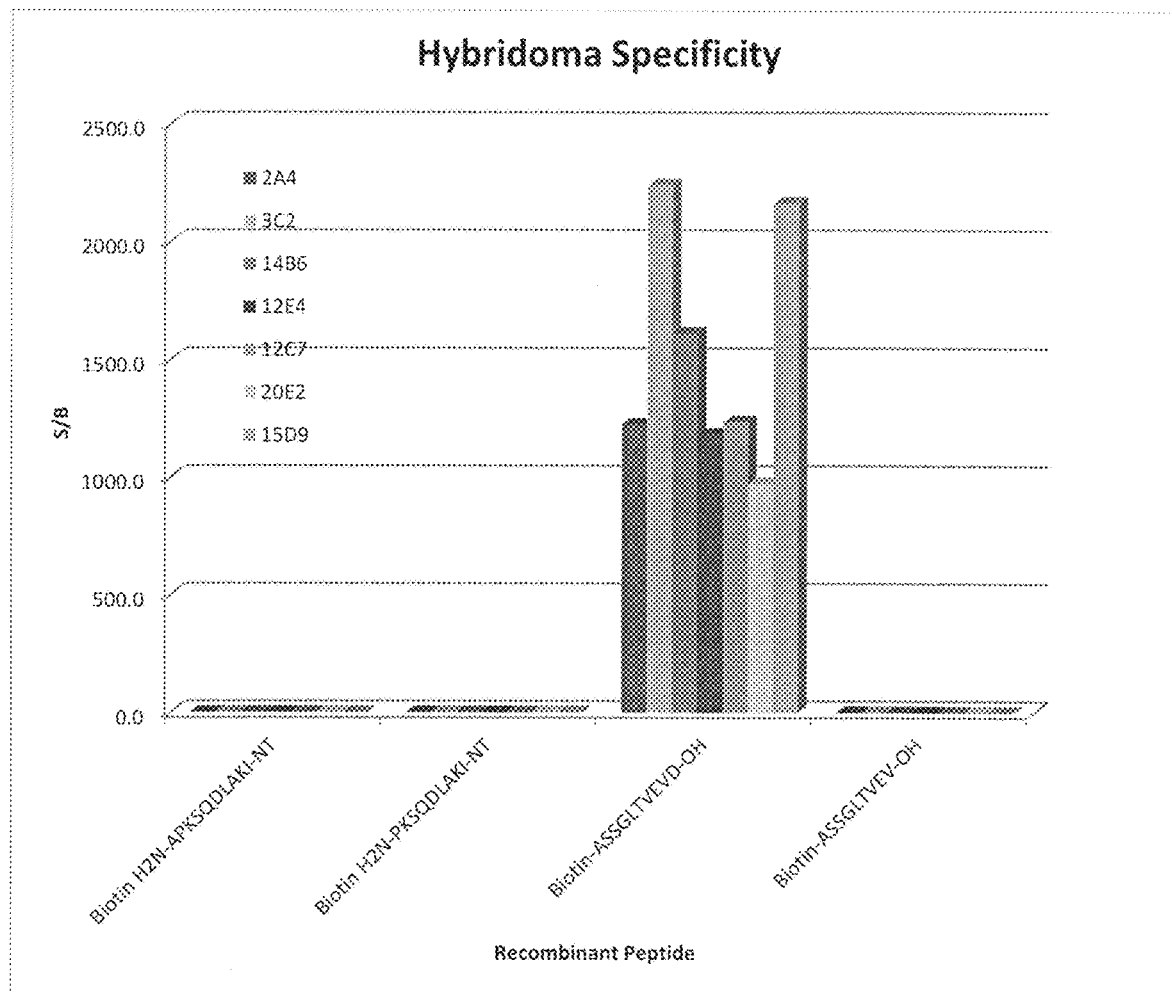
FIG. 2 is a graphical illustration of hybridoma specificity tested for antibodies disclosed herein.

FIG. 2 provides a graphical illustration of the specificity of hybridoma cell lines producing antibodies with positive response to peptide P1. Cell lines 2A4, 3C2, 14B6, 12E4, 12C2, 20E3 and 15D9 were found to be specific for the sequence $^{229}$ASSGLTVEVD (SEQ ID NO:1) and negative for peptide sequences $^{229}$ASSGLTVEV (SEQ ID NO:12), $^{239}$APKSQDLAKI (SEQ ID NO:10) and $^{240}$PKSQDLAKI (SEQ ID NO:11) (See, e.g., FIG. 2).

Example 2—Characterization of Monoclonal Antibody 3C2

Figure 3:
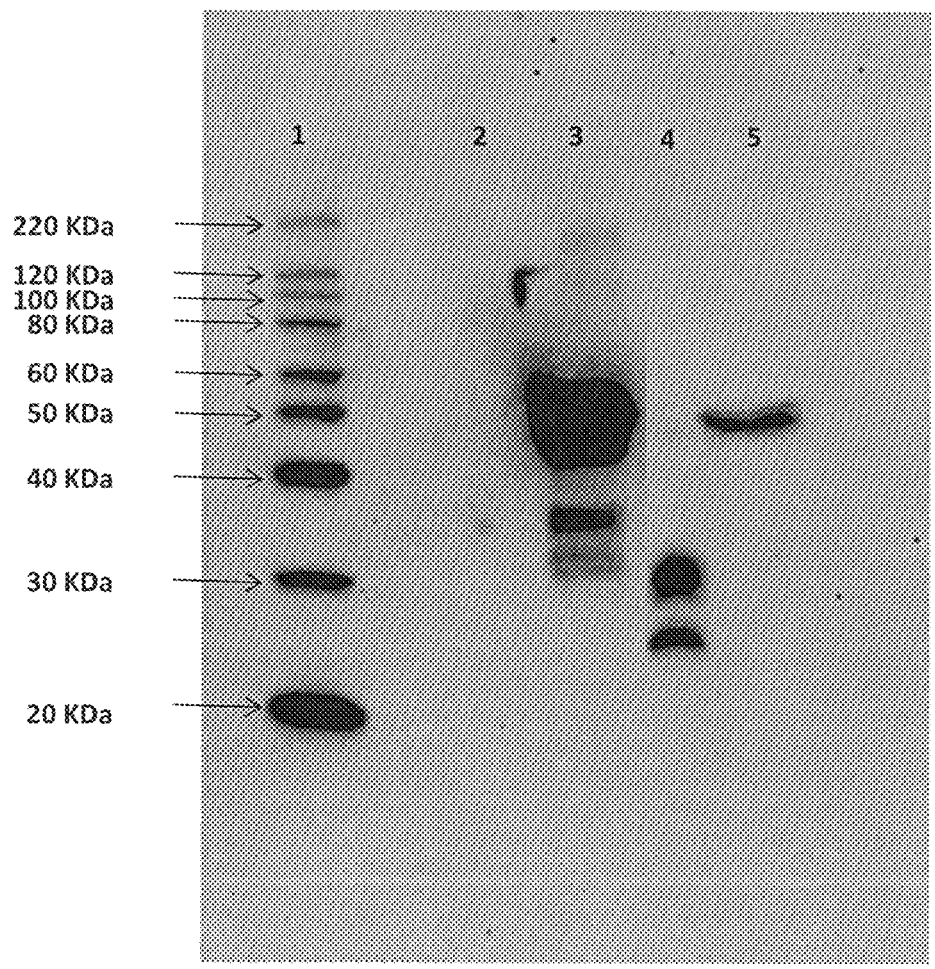
FIG. 3 is a photographic representation of a Western Blot Analysis with a commercially available monoclonal antibody (mAb) C-04.

Monoclonal antibodies 3C2 and C-04 were characterized by Western blot analysis against full length recombinant cytokeratin 18 protein (rCK18) and a cell extract of apoptotic SK-BR3 cells (human breast cancer cell line induced to become apoptotic). FIG. 3 is a photographic reproduction of a Western Blot Analysis using a commercially available monoclonal antibody C-04 (Sigma-Aldrich®, SAB4700411-100UG) (Lane 1, marker proteins; Lane 2, blank; Lane3, 1 µg recombinant full length CK18 protein (rCK18); Lane 4, 12 µL of SK-BR3 cell apoptotic supernatant; Lane 5, 12 µL of SK-BR3 cell supernatant). Proteins were run in a 14% Tris/Glycine gel. The concentrations for the test material were 1 µg of rCK18 and 12 µL of SK-BR3 apoptotic supernatant and SK-BR3 cell lysate. The proteins were run at 150V constant until the dye front reached the end of the gel. The proteins were then transferred to nitrocellulose. The nitrocellulose was blocked and then probed with the C-04 mAb at 1 µg/mL for 60 minutes. The membrane was then washed three times. The membrane was then probed with a goat anti-mouse IgG ALK for 30 minutes. The membrane was washed three times and developed using a WesternBreeze® kit from Invitrogen™ (Cat #WB7104). Monoclonal antibody C-04, specific for human cytokeratin 18 protein, detected rCK18 (See FIG. 3, lane 3), full length CK18 from a cell extract of SK-BR-3 cells (See FIG. 3, Lane 5), human CK18 protein fragment M1-D238 (SEQ ID NO:4) (See FIG. 3, lane 4) and two additional smaller fragments.

Figure 4:
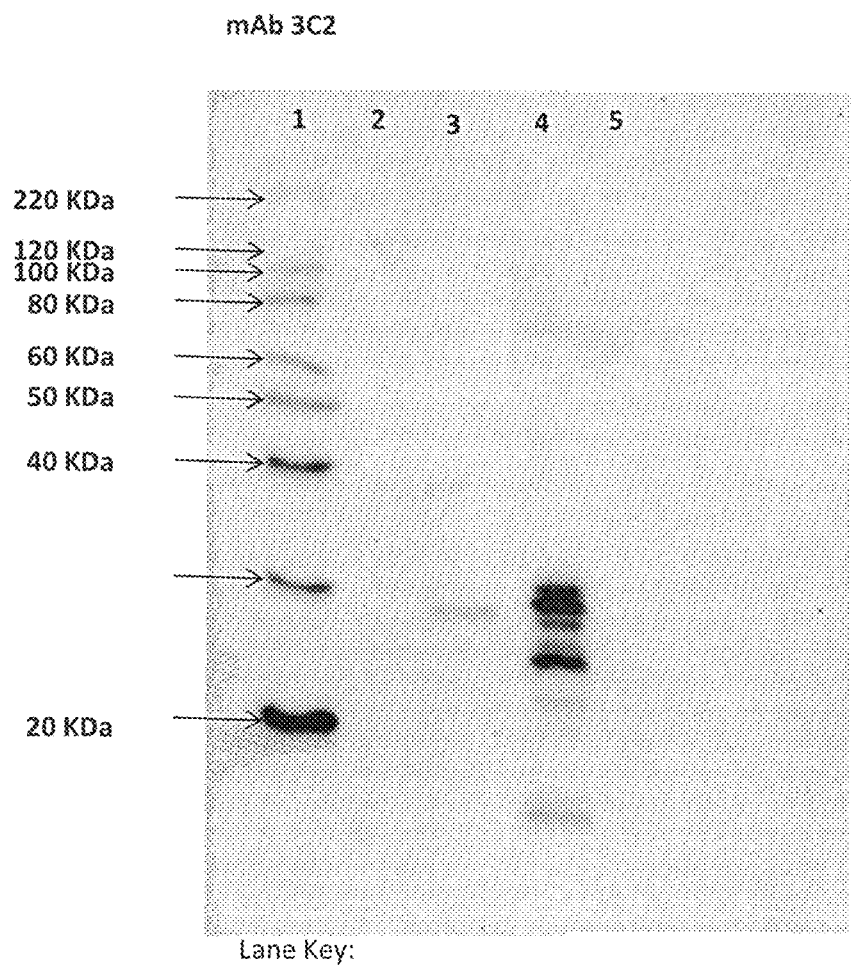
FIG. 4 is a photographic representation of a Western Blot Analysis with mAb 3C2.

FIG. 4 is a photographic reproduction of a Western Blot Analysis using the mAb 3C2 (Lane 1, marker proteins; Lane 2, blank; Lane 3, 1 µg recombinant full length CK18 protein (rCK18); Lane 4, 12 µL of SK-BR3 apoptotic cell supernatant; Lane 5, 12 µL of SK-BR3 cell supernatant). Proteins were run in a 14% Tris/Glycine gel. The concentrations for the test material were 1 µg of rCK18 and 12 µL of SK-BR-3 apoptotic supernatant and SK-BR-3 Cell Lysate. The proteins were run at 150 V constant until the dye front reached the end of the gel. The proteins were then transferred to nitrocellulose. The nitrocellulose was blocked and probed with the 3C2 mAb at 1 µg/mL for 60 minutes. The membrane was washed three times and probed with a goat anti-mouse IgG ALK for 30 minutes. The membrane was washed three times and developed with using a WesternBreeze® kit from Invitrogen™ (Cat #WB7104). The results indicated that mAb 3C2 did not bind to full length rCK18 protein (See FIG. 4, lane 3) or to full length recombinant CK18 protein (See FIG. 4, lane 5) and did detect the presence of human CK18 protein fragment M1-D238 (SEQ ID NO:4) as well as smaller protein fragments which may be degradation products of this fragment (See FIG. 4, lane 4).

The specificity of monoclonal antibody 3C2 was also assessed in an immunoassay against the peptides $^{229}$ASSGLTVEVD (SEQ ID NO:1), $^{229}$ASSGLTVEV (SEQ ID NO:12) and $^{388}$EDFNLGDALD (SEQ ID NO:13) (each conjugated with biotin at their amino-terminus), which were added to a 96-well microplate coated with NeutrAvidin® by Invitrogen™. Human cytokeratin 18 protein fragment A239-D397 was also produced by the action of caspase 3 during cellular apoptosis and ends in the sequence $^{394}$DALD (SEQ ID NO:9). These peptides were incubated with mAb 3C2, M30 antibody (Enzo Life Sciences®, ALX-804-590) or other unrelated mAbs.

Figure 5:
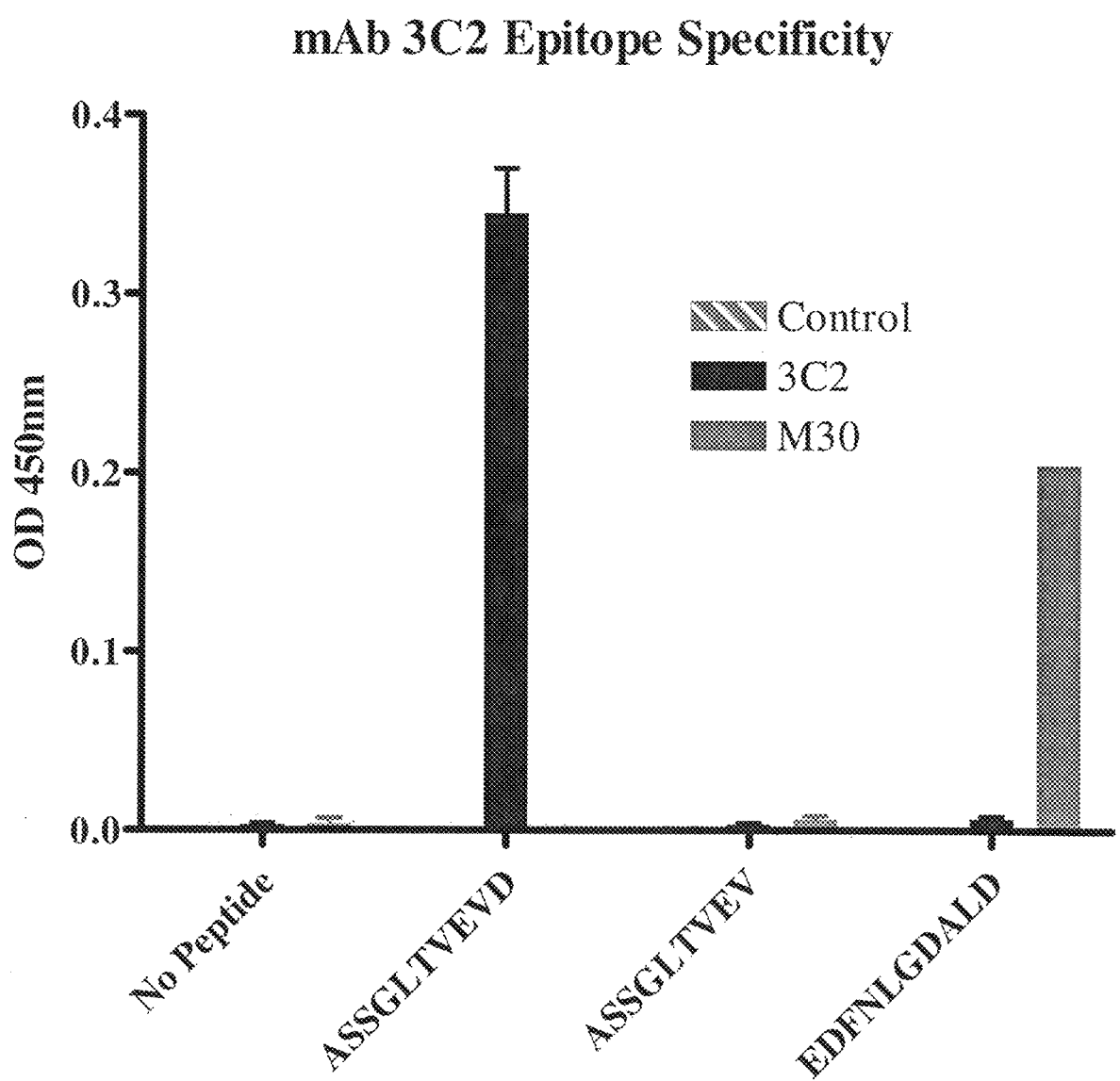
FIG. 5 is a graphical illustration of antibody epitope specificity for antibodies disclosed herein.

FIG. 5 provides a graphical representation of the antibody specificity for the antibodies discussed above. The results summarized in the graph of FIG. 5, indicated that mAb 3C2 specifically bound to the peptide ending in $^{235}$VEVD (SEQ ID NO:2) and did not bind to the peptides ending in $^{235}$VEV or $^{394}$DALD (SEQ ID NO:9), while the M30 antibody bound to the peptide ending in $^{394}$DALD (SEQ ID NO:9) but did not bind to the peptides ending in $^{235}$VEVD (SEQ ID NO:2) or $^{235}$VEV.

Example 3—Amino Acid and Nucleotide Sequences of the Variable Regions of the Heavy and Light Chains of mAb 3C2

Sequences were obtained using standard procedures by LakePharma of Belmont, Calif. Total RNA was extracted from hybridoma cells. RACE (Rapid Amplification of cDNA Ends) was performed to amplify DNA for variable heavy ($V_H$) and variable light ($V_L$) chains. Positive clones were identified by gel electrophoresis. Positive DNA was cloned and sequenced. The DNA was analyzed and the amino acid sequences for $V_H$ and $V_L$ were presented.

The amino acid sequence of the variable region of the heavy chain of mAb 3C2 was determined to be: DVQLVESGGG LVQPGGSRKL SCAASGFTFS SFGMHWVRQA PEKGLEWVAY INGGSTIIYY ADTVKGRFTV SRDNPKNTLF LQMTSLRSDD TAMYFCVRRT PTAAGGAMDY WGQGTSVTVS S (SEQ ID NO:5).

The nucleotide sequence coding for the variable region of the heavy chain of mAb 3C2 was determined to be: gatgtgcagc tggtggagtc tgggggaggc ttagtgcagc ctggagggtc ccggaaactc tcctgtgcag cctctggatt cactttcagt agttttggaa tgcactgggt tcgtcaggct ccagagaagg ggctggaatg ggtcgcatac attaatggtg gcagtaccat catctactat gcagacacag tgaagggccg attcaccgtc tccagagaca atcccaagaa caccctgttc ctgcaaatga ccagtctaag gtctgacgac acggccatgt atttttgtgt aagaaggacc cctacggctg cggggggggc tatggactat tggggtcaag gaacctcagt caccgtctcc tca (SEQ ID NO:6).

The amino acid sequence of the variable region of the light chain of mAb 3C2 was determined to be: NIMVTQSPSS LAVSAGEKVT MTCKSSQSLF YSSNQKNYLA WFQQKPGQSP KLLIYWASTR ESGVADRFTG SGYGTDFTLT ISSVQAEDLA VYYCQQYLSS WTFGGGTKVE IK (SEQ ID NO:7).

The nucleotide sequence coding for the variable region of the light chain of mAb 3C2 was determined to be: aacattatgg tgacacagtc gccatcatct ctggctgtgt ctgcaggaga aaaggtcact atgacctgta agtccagtca aagtcttttc tacagttcaa accagaagaa ctacttggcc tggttccagc agaaaccagg gcagtctcct aaactgctga tctactgggc atccactagg gagtctggtg tcgctgatcg cttcacaggc agtggatatg ggacagattt tactctaacc atcagcagtg tacaggccga agacctggca gtttattact gtcaacaata cctctcgtct tggacgttcg gtggaggtac caaggtggaa atcaaac (SEQ ID NO:8).

Example 4—Specificity for Caspase-Cleaved Cytokeratins

Assay specificity was examined using full length recombinant CK18 (Fitzgerald Cat. #30R-2135), CK14 (Fitzgerald Cat. #30R-2140), CK18 (Fitzgerald Cat. #30R-2139), CK19 (Fitzgerald Cat. #30R-2136), and CK20 (Fitzgerald Cat. #30R-2142). The cytokeratins were used at 150 ng/mL of fragmented material spiked into normal human serum and tested in the CK18 assay.

To prepare fragmented material the full length cytokeratins were treated with Caspase-3 (Sigma-Aldrich®, Cat. #C1224) by adding 10 μL of 1 mg/mL stock cytokeratin to 50 μL of buffer (50 mM Hepes, 100 mM NaCl, 5% (w/v) glycerol, 0.5 mM EDTA, 0.05% w/v CHAPs and 5 mM DTT, pH 7.3) and treated with 1 μL of recombinant Caspase-3 (0.2 μg/mL) for 2 hours at 37° C. After caspase-3 treatment material was diluted to 150 ng/mL in normal serum and evaluated.

The capture mAb 3C2 was biotin-conjugated and pre-bound to streptavidin coated paramagnetic beads (See, e.g., FIG. 1). The detector mAb C-04 was TAG-conjugated. Fifty microliters of calibrators (0-100,000 U/L), controls (High, Medium, Low), normal human serum spiked with 150 ng/mL fragmented cytokeratins and normal human serum spiked with 150 ng/mL full length cytokeratins were combined with 50 μL of a master mix consisting of equal volumes of capture and detector reagents in a 96 well microplate and incubated for 60 minutes at room temperature with shaking. The plate was washed and read on an ECL analyzer.

The results show that the assay only produced signal with the caspase-3-cleaved (treated) CK-18 and not with the other four caspase-3-cleaved (treated) cytokeratins or the full-length (untreated with caspase-3) cytokeratins. Table 1 contains the determined concentration results for the full-length (untreated) cytokeratins and cleaved (caspase-3-treated) cytokeratins. The data shows that the mAb 3C2 does not bind to full-length or caspase-3-cleaved cytokeratins 8, 14, 19 and 20.

TABLE 1

| Specificity Samples | Full Length (Untreated) Mean (U/L) | Cleaved (Caspase-3-Treated) Mean (U/L) |
|---|---|---|
| CK-8 | ND | ND |
| CK-14 | ND | ND |
| CK-18 | ND | 176 |
| CK-19 | ND | ND |
| CK-20 | ND | ND |

ND = Not Detected

Example 5—Human CK18 Protein Fragment B (rCK18fB) Assay

A recombinant human CK18 protein fragment B (rCK18fB) was prepared using standard procedures. An immunoassay consisted of incubating 50 μL rCK18fB (0, 206, 617, 1852, 5557, 16667, 50,000 and 100,000 U/L) spiked into normal human serum with 50 μL of reaction mix consisting of biotinylated mAb 3C2/streptavidin coated paramagnetic beads and anti-CK18 TAG labeled antibody C-04 for 60 minutes at room temperature with shaking. The bead complex was washed twice, suspended in buffer and read on an ECL analyzer. The results shown in FIG. 6, a representative standard curve, indicate rCK18fB is detectable over a range of 0-100,000 U/L (1 U/L=1000 pg=0.037 pM).

Figure 6:
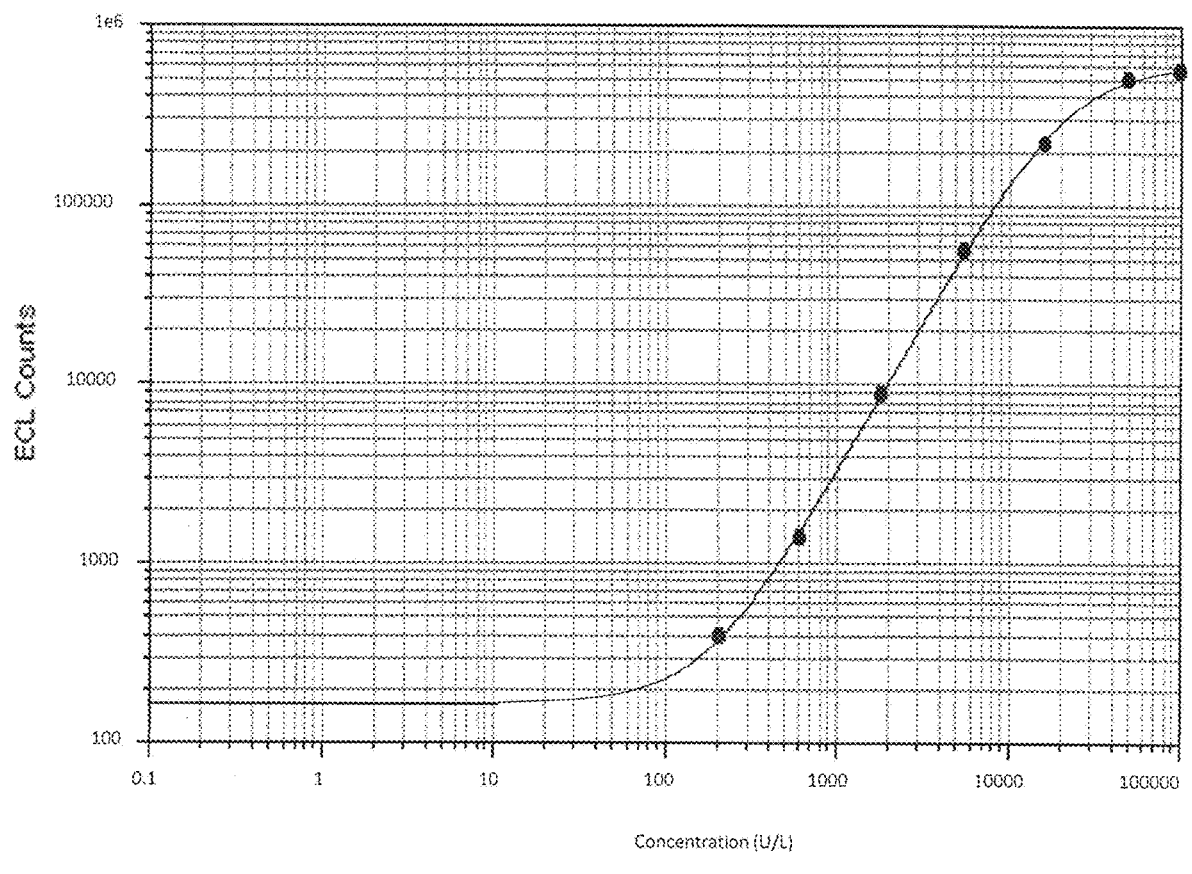
FIG. 6 is a graphical representation of the detection of a recombinant CK18 fragment B (rCK18fB) which serves as a representative standard curve for the methods described in Example 5.
Figure 7:
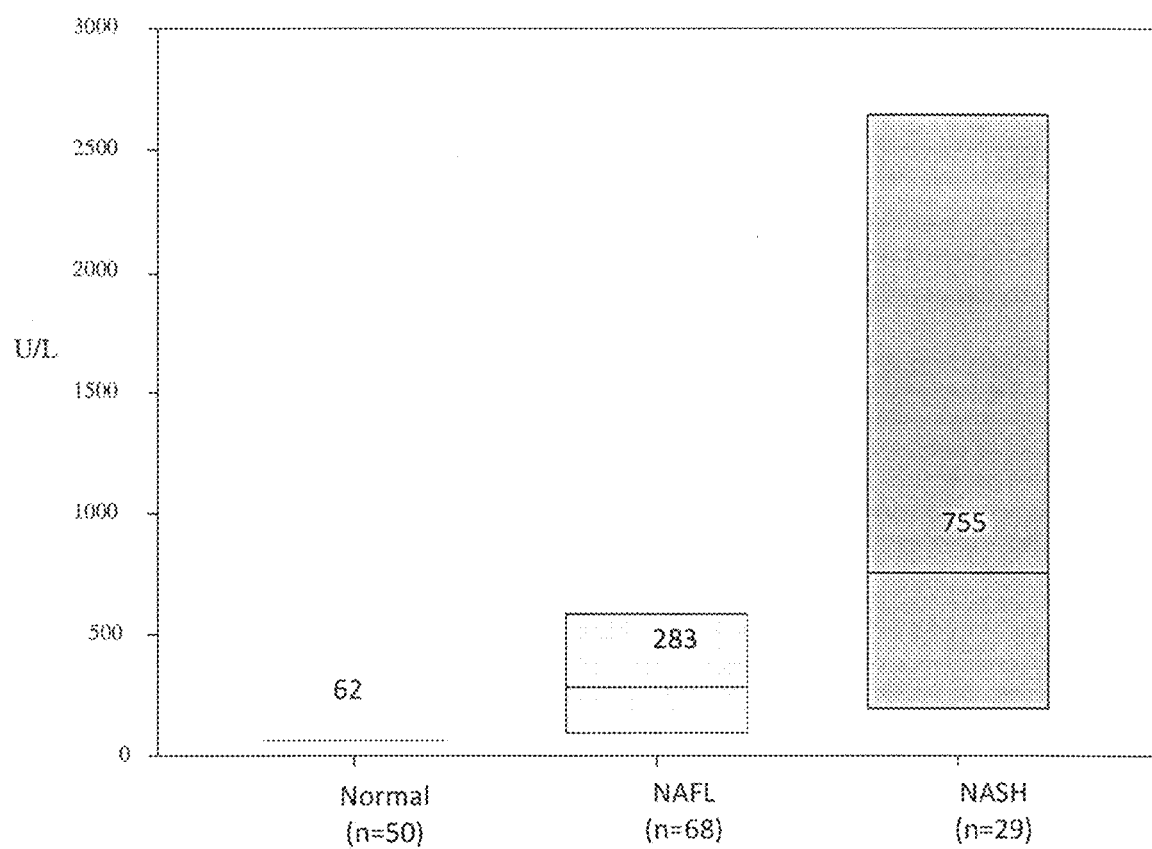
FIG. 7 is a graphical representation of the evaluation of normal, NAFL and NASH samples as described in Example 6.

Example 6—Detection of Human Cytokeratin 18 Protein Fragments in NAFL and NASH Cytokeratin 18 protein fragments having C-terminus VEVD$^{238}$ (SEQ ID NO:2) present in human plasma samples with known NAFL and NASH status were quantified using a rCK18fB standard curve, for example, as shown in FIG. 6. Nonalcoholic fatty liver disease (NAFLD) is a spectrum of disorders characterized by hepatic steatosis, which may be benign (NAFL) or which may progress via inflammation and fibrosis to nonalcoholic steatohepatitis (NASH) and then to cirrhosis and liver failure. Liver biopsy is the standard diagnostic approach for NAFL/NASH. However it has limitations due to sampling site variability, cost and procedure-related morbidity. Appropriate NAFLD-specific circulating biomarkers may enable diagnosis, staging and monitoring of NAFL/NASH with fewer biopsies. Commercial human serum samples (50 normal, 68 NAFL and 29 NASH) were obtained from ProMedDx and BioreclamationIVT. The samples and rCK18fB protein (50 μL) were incubated as described in Example 5. The results (See, e.g., FIG. 7) indicated that the normal, NAFL and NASH samples were each readily quantified by the assay method (62, 288, and 755 U/L, respectively).

Example 7—Human CK18 Protein Fragment B Capture and Detector Antibody Orientation The sensitivity of the immunoassay was assessed with respect to the use of mAb C-04 in conjunction with the VEVD (SEQ ID NO:2) specific mAb 3C2 by evaluating the orientation of the antibodies used to either capture or detect cytokeratin 18 protein fragments ending in the sequence VEVD (SEQ ID NO:2) including: a) Capture 3C2 with Detector C-04; and b) Capture C-04 with Detector 3C2.

The capture mAb was biotin-conjugated and pre-bound to streptavidin coated paramagnetic beads. The detector mAb was TAG-conjugated. The working concentration of pre-bound capture mAb beads was 0.2 mg/mL and the working concentration of TAG-conjugated detector mAb was 5 μg/mL. The antibody orientation was evaluated with recombinant CK-18 fragment B protein (rCK18fB) and with a cell lysate from SK-BR-3 cells treated with 50 μM of cisplatin for 48 hours to induce apoptosis. Samples (50 μL) of rCK18fB (0-150,000 pg/mL in normal serum) and SK-BR-3 cell lysate (diluted from 1:2 to 1:128 by serial dilution in Antibody Diluent) were combined with 50 μL of a master mix consisting of equal volumes of capture and detector reagents (representing each of the four capture and detector mAb pairs) in a 96 well microplate and incubated for 60 minutes at room temperature with shaking. The plate was washed and read on an ECL analyzer.

Figure 8:
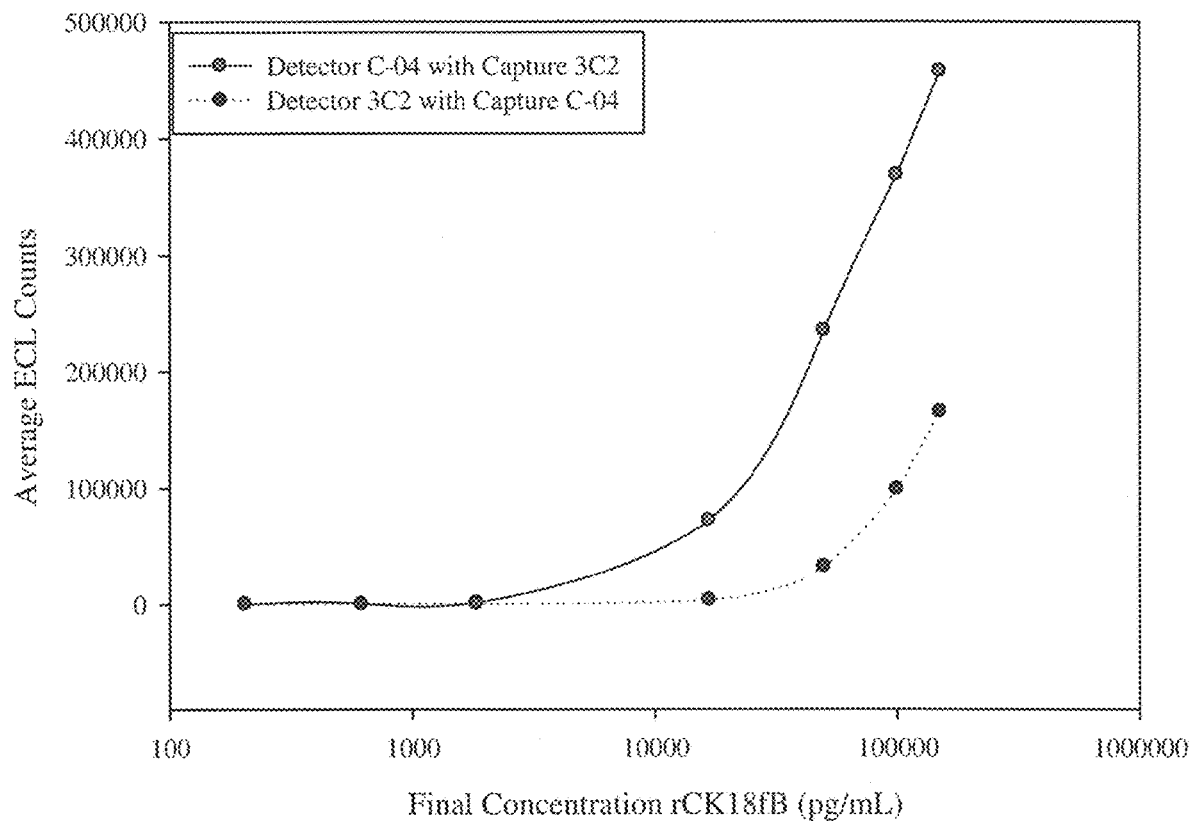
FIG. 8 is a graphical representation of a curve prepared with rCK18fB, according to the methods disclosed herein.
Figure 9:
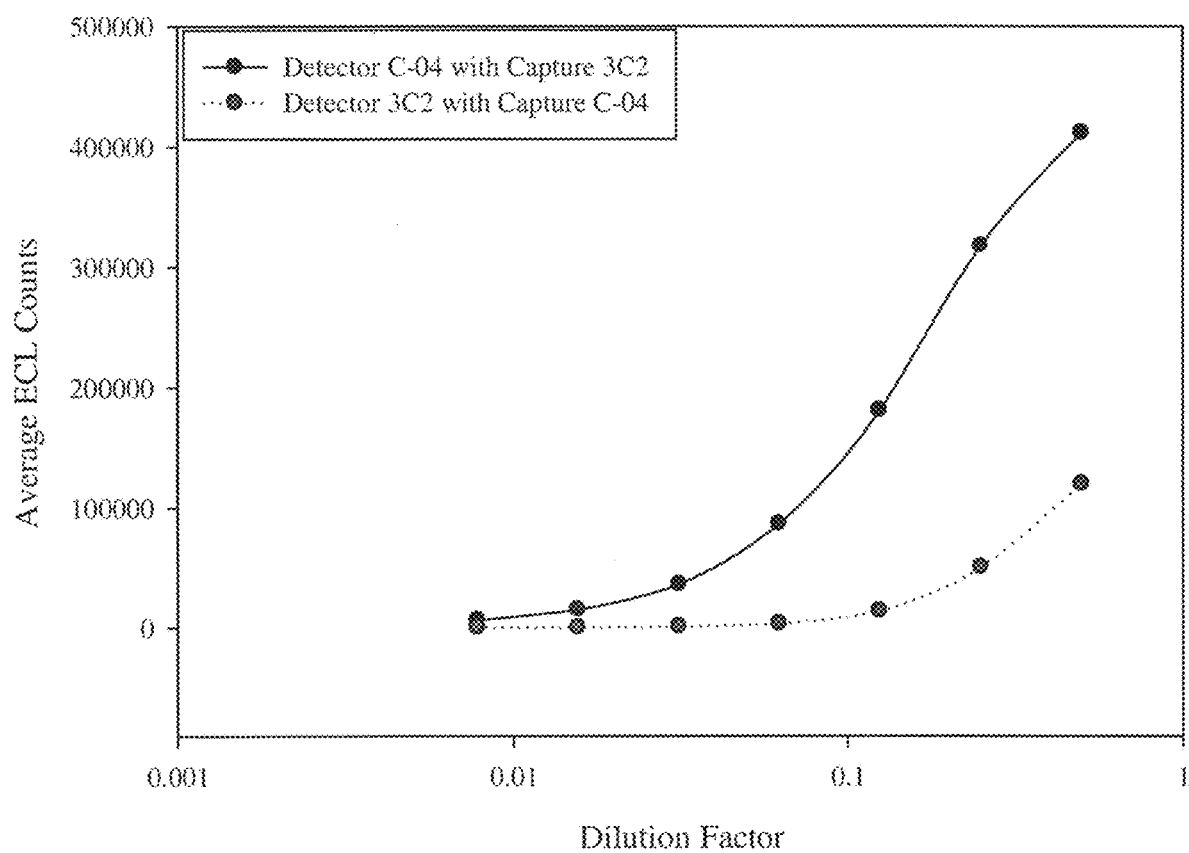
FIG. 9 is a graphical representation of a curve prepared with SK-BR3 Apoptotic Supernatant according to the methods disclosed herein.

FIG. 8 provides a graphical representation of a curve prepared using the format with mAb 3C2 as the detector antibody for the CK18 assay with rCK18fB. FIG. 9 provides a graphical representation of a curve prepared using the format with mAb 3C2 as the detector antibody for the CK18 assay with Apoptotic SK-BR3 Supernatant. The results clearly indicated that the format using mAb 3C2 as the capture antibody was more sensitive than the format using mAb 3C2 as the detector antibody (See, e.g., FIGS. 8 and 9), with at least a 0.5 log increase in sensitivity achieved.

The examples disclosed herein are merely illustrative and intended to be non-limiting. Moreover, it should be understood that various features and/or characteristics of differing embodiments herein may be combined with one another. It is therefore to be understood that numerous modifications may be made to the illustrative embodiments and that other arrangements may be devised without departing from the scope of the present disclosure. Other embodiments will be apparent to those skilled in the art from consideration of the disclosure and practice of the various example embodiments disclosed herein. It is intended that the specification and examples be considered as examples only, with the true scope of the invention being indicated by the claims.

It is also to be understood that, as used herein the terms "the," "a," or "an," mean "at least one," and should not be limited to "only one" unless explicitly indicated to the contrary. Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points within the example ranges and values provided. Efforts have been made to ensure the accuracy of the numerical values disclosed herein. Any measured numerical value, however, can inherently contain certain errors resulting from the standard deviation found in its respective measuring technique.

All publications, patents and patent applications mentioned in this specification are herein incorporated by reference in their entirety into the specification to the same extent as if each individual publication, patent or patent application was specifically and individually indicated to be incorporated herein by reference. Also incorporated by reference is any supplemental information that was published along with any of the aforementioned publications, patents and patent applications. For example, some journal articles are published with supplemental information that is typically available online.

What is claimed is:

1. An antibody wherein the antibody has binding specificity to the amino acid sequence Ala Ser Ser Gly Leu Thr Val Glu Val Asp (SEQ ID NO:1), wherein the antibody comprises a variable region of the heavy chain amino acid sequence of SEQ ID NO:5, and a variable region of the light chain amino acid sequence of SEQ ID NO:7.

2. The antibody of claim 1, wherein the antibody is coupled to a solid support or a detection moiety.

3. The antibody of claim 2, wherein the antibody is directly bound to the solid support or the detection moiety.

4. The antibody of claim 2, wherein the antibody is indirectly bound to the solid support or the detection moiety.

5. The antibody of claim 2, wherein the detection moiety is selected from the group consisting of electrochemiluminescence labels or compounds, chemiluminescent compounds, enzyme labels, fluorophores, chromogenic compounds, radiolabels, catalysts, colorimetric, labeled antibodies, a latex particle, a magnetic particle, a paramagnetic particle, a radioactive element, fluorescent dyes, phosphorescent dyes, dye crystals, gold particles, silver colloidal particles, selenium colloidal particles, metal chelates, coenzymes, electro active groups, oligonucleotides and stable radicals.

6. The antibody of claim 5, wherein the metal chelate is a ruthenium, an osmium, or a europium metal chelate.

7. The antibody of claim 2, wherein the solid support is selected from the group consisting of a bead, a plate, a glass surface, a plastic surface, a metal surface, a polystyrene surface, a nitrocellulose surface, a microparticle and a nanoparticle surface.

8. The antibody of claim 7, wherein the solid support is a bead.

* * * * *